US00PP27189P2

(12) United States Plant Patent
Zaiger et al.

(10) Patent No.: US PP27,189 P2
(45) Date of Patent: Sep. 27, 2016

(54) INTERSPECIFIC TREE NAMED 'TRINIDAD'

(50) Latin Name: ***Interspecific Prunus* species**
Varietal Denomination: Trinidad

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 44 days.

(21) Appl. No.: 14/545,006

(22) Filed: Mar. 16, 2015

(51) Int. Cl.
*A01H 5/08* (2006.01)

(52) U.S. Cl.
USPC ..... Plt./180

(58) Field of Classification Search
USPC ..... Plt./180
See application file for complete search history.

*Primary Examiner* — Anne Grunberg

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with a vigorous, semi-spreading growth habit.
2. Tree being a regular and productive bearer of medium to large size fruit.
3. Fruit with good flavor and eating quality.
4. Fruit with an orange skin color and attractive red blush.
5. Fruit with good storage and shipping quality.

1 Drawing Sheet

Botanical designation: Interspecific *Prunus* species.
Variety denomination: 'Trinidad'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of interspecific trees, which are known to us, and mentioned herein, 'Leah Cot' Interspecific (U.S. Plant Pat. No. 21,863), 'Betty-Cot' Interspecific (U.S. Plant Pat. No. 22,648) and our proprietary non-patented interspecific seedling selections '15MA725', '160LH337' and '28Z198'.

STATEMENT REGARDING FEDERALLY SPONSORED RESEARCH AND DEVELOPMENT

Not applicable.

ORIGIN OF THE VARIETY

The new and distinct interspecific tree consists of is a combination of crosses between (*Prunus armeniaca* and

*Prunus salicina*). The new seedling was originated by us in our experimental orchard located near Modesto, Calif. as a first generation cross between our proprietary non-patented interspecific seedling with the field identification number '15MA725' and 'Leah Cot' Interspecific (U.S. Plant Pat. No. 21,863). The proprietary non-patented interspecific seed parent (15MA725) originated from a cross between our proprietary non-patented apricot seedling '160LH337' with our proprietary non-patented interspecific seedling '28Z198'. A large number of these first generation seedlings were grown and budded onto older established trees of 'Nemaguard' Rootstock (non-patented) to enhance earlier fruit production. Under close and careful observation, the present budded seedling exhibited desirable fruit and tree characteristics and was selected in 2009 for additional asexual propagation and commercialization.

ASEXUAL REPRODUCTION OF THE VARIETY

In 2009 asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of interspecific tree (*Prunus armeniaca*×*Prunus salicina*) is of large size, vigorous, semi-spreading growth and is a regular and productive bearer of medium size, yellow/orange flesh, freestone fruit with good flavor and eating quality. The fruit is further characterized by having orange skin color with an attractive red blush and having good handling and storage abilities. In comparison to its non-patented interspecific seed parent (15MA725) the fruit of the new variety is larger in size. In comparison to its pollen parent 'Leah Cot' Interspecific (U.S. Plant Pat. No. 21,863) the fruit of the new variety has a lower winter chilling requirement of 300 hours compared to 850 hours and is approximately 24 days earlier in maturity. In comparison to the commercial variety 'Betty-Cot' Interspecific (U.S. Plant Pat. No. 22,648) the fruit of the new variety has a lower winter chilling requirement of 300 hours compared to 750 hours and is approximately 10 days earlier in maturity.

DESCRIPTION OF THE PHOTOGRAPH

The accompanying color photographic illustration shows typical specimens of the foliage and fruit of the present new interspecific variety.

The illustration shows the upper and lower surface of the leaves, an exterior and sectional view of a single fruit divided in its suture plane to show flesh color, pit cavity and the stone remaining in place.

The photographic illustration was taken shortly after being picked (shipping ripe) from a 7 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 7 year old specimens grown near Modesto, Calif., with color in accordance with Munsell Book of Color published in 1958.

Tree:

*Size*.—Large, usually pruned to 3 to 3.5 meters in height and width for economical harvesting of fruit. Size varies with different cultural practices.

*Vigor*.—Vigorous, growth of 1.5 to 2 meters in height the first growing season. Varies with type of soil, fertility and cultural practices.

*Form*.—Semi-spreading, usually pruned to vase shape.

*Branching habit*.—Semi-spreading, crotch angle approximately 30°, increases with heavy crop load.

*Productivity*.—Productive, thinning and spacing of fruit necessary for desired market size fruit. Number of fruit set varies with climatic conditions during blooming period.

*Bearer*.—Regular, has had adequate fruit set 5 consecutive years. No alternate bearing observed.

*Fertility*.—Self fertile, set fruit under the bag.

*Density*.—Medium dense, usually pruned to vase shape to increase air movement and sunlight to enhance fruit color and health of fruit spurs.

*Hardiness*.—Hardy in all stone fruit growing areas of California. Tree grown in USDA Hardiness Zone 9. Winter chilling requirement approximately 300 hours at or below 45° F.

Trunk:

*Size*.—Large. Average circumference of 68.6 cm at 27.9 cm above ground on a 7 year old tree.

*Stocky*.—Medium stocky.

*Texture*.—Medium shaggy, roughness increases with age.

*Color*.—Varies from 5YR 2/4 to 7.5YR 3/2.

Branches:

*Size*.—Medium. Average circumference 16.0 cm at 1.2 meters above ground.

*Surface texture*.—New growth relatively smooth. Mature growth medium rough, roughness increases with age.

*Lenticels*.—Average number 33 in a 25.8 square cm area. Average length 4.1 mm. Average width 2.1 mm. Color varies from 5Y 8/6 to 5Y 7/10.

*Color*.—New growth varies from 5GY 4/8 to 10R 3/3. Mature growth varies from 7.5YR 3/4 to 7.5YR 2/4, varies with age of growth.

Leaves:

*Size*.—Medium to large. Average length 87.8 mm. Average width 68.1 mm.

*Form*.—Ovate.

*Apex*.—Acuminate.

*Base*.—Cuneate.

*Margin*.—Double serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 36.5 mm. Average width 1.6 mm. Longitudinally grooved. Surface — glabrous. Color varies from 5GY 5/6 to 7.5R 2/6.

*Glands*.—Type — globose. Size — small to medium. Average length 0.9 mm. Average diameter 0.7 mm. Number varies from 1 to 5, average number 3. Located primarily on upper portion of petiole and base of leaf blade. Color varies from 5GY 5/6 to 7.5R 3/10.

*Stipules*.—Average number 2. Average length 9.9 mm. Edges — pectinate. Color varies from 2.5GY 6/8 to 7.5R 3/12.

*Color*.—Upper surface varies from 5GY 4/4 to 5GY 3/4. Lower surface varies from 2.5GY 4/6 to 5GY 4/4. Midvein color varies from 5GY 6/6 to 7.5R 3/12.

Flower buds:

*Size*.—Medium to large. Average length 16.0 mm. Average diameter 9.1 mm.

*Hardiness*.—Hardy with respect to California winters.

*Density*.—Medium dense.

*Form*.—Conical, becoming elongated just before opening.

*Pedicel*.—Average length 2.0 mm. Average width 2.1 mm. Color varies from 2.5Y 9/4 to 2.5Y 8.5/4. Surface glabrous.

*Color*.—Varies from 10P 9/2 to 5RP 8/4.

*Number of buds per spur*.—Varies from 8 to 15, average number 12. Varies with age of spur.

Flowers:

*Blooming period*.—Date of First Bloom Feb. 7, 2014. Date of Petal Fall Feb. 17, 2014, varies slightly with climatic conditions.

*Size*.—Medium to large. Average height 17.8 mm. Average diameter 25.6 mm.

*Petals*.—Normally 5, alternately arranged to sepals. Petal apex — rounded. Petal base — rounded to somewhat truncated. Size — medium to large. Average length 13.6 mm. Average width 13.0 mm. Form — orbicular. Arrangement — overlapping.

Margin — sinuate. Color varies from 5RP 9/2 to 7.5RP 9/2, fades with age of flower. Both upper and lower surfaces glabrous.

*Sepals*.—Normally 5, alternately arranged to petals. Size — medium to large. Average length 7.1 mm. Average width 5.3 mm. Shape — triangular. Apex rounded to triangular. Margin — entire. Both upper and lower surfaces glabrous. Color — upper surface varies from 10RP 3/8 to 10RP 3/6. Lower surface varies from 10RP 8/2 to 7.5RP 7/2.

*Stamens*.—Average number per flower 31. Average filament length 12.1 mm. On average, the stamens are above the height of the petals. Filament color N 9.5/ (white). Anther color varies from 2.5Y 8/12 to 5Y 8/12.

*Pollen*.—Self fertile, set fruit under the bag. Color varies from 2.5Y 7/10 to 10YR 7/10.

*Pistil*.—Number — normally 1. Average length 15.2 mm. Position of stigma an average of 1.5 mm below anthers. Surface pubescent. Color varies from 1Y 8.5/4 to 10Y 8/4.

*Fragrance*.—Heavy.

*Color*.—Varies from 5RP 9/2 to 7.5RP 9/2.

*Pedicel*.—Average length 2.5 mm. Average width 2.1 mm. Color varies from 7.5Y 8/6 to 7.5Y 8/4.

*Number flowers per flower bud*.—Average 3, varies from 2 to 5.

Fruit:

*Maturity when described*.—Firm ripe and ready for consumption.

*Date of first picking*.—May 17, 2014.

*Date of last picking*.—May 27, 2014, varies slightly with climatic conditions.

*Size*.—Medium to large. Average diameter axially 54.8 mm. Average transversely in suture plane 59.0 mm. Average across suture plane 57.3 mm. Average weight 99.4 grams, varies slightly with fertility of the soil, amount of thinning and climatic conditions.

*Form*.—Globose to slightly elongated.

*Suture*.—Lipped.

*Ventral surface*.—Lipped.

*Apex*.—Slightly retuse.

*Base*.—Retuse.

*Stem cavity*.—Rounded to slightly elongated in suture plane. Average depth 6.6 mm. Average diameter 5.8 mm.

Stem:

*Size*.—Small. Average length 6.9 mm. Average diameter 3.9 mm.

*Color*.—Varies from 10Y 6/8 to 2.5GY 6/8.

Flesh:

*Ripens*.—Evenly.

*Texture*.—Firm, meaty.

*Fibers*.—Few, small, tender.

*Firmness*.—Firm, comparable to other commercial apricot varieties.

*Aroma*.—Heavy.

*Amydgalin*.—Undetected.

*Eating quality*.—Good.

*Flavor*.—Good.

*Juice*.—Moderate amount, enhances flavor.

*Acidity*.—Not available.

*Brix*.—Average Brix of 16.0°, varies slightly with amount of fruit per tree and climatic conditions.

*Color*.—Varies from 7.5Y 8/4 to 7.5Y 7/10.

*Pit cavity*.—Average length 30.0 mm. Average width 24.7 mm. Average depth 8.0 mm. Color varies from 5YR 6/10 to 5YR 5/10.

Skin:

*Thickness*.—Medium.

*Surface*.—Very slightly waffled.

*Pubescence*.—Moderate pubescence, short in length.

*Tendency to crack*.—None.

*Color*.—Ground color varies from 7.5YR 7/10 to 7.5YR 7/12. Partially overspread with 7.5R 5/12 to 7.5R 4/12.

*Tenacity*.—Tenacious to flesh.

*Astringency*.—Undetected.

Stone:

*Type*.—Freestone, almost no adherence.

*Size*.—Large. Average length 27.1 mm. Average width 21.7 mm. Average thickness 13.6 mm.

*Form*.—Obovoid.

*Base*.—Flat.

*Apex*.—Rounded.

*Surface*.—Slightly pitted throughout, a shallow groove on each side of suture extending from base to apex.

*Sides*.—Unequal, one side extending further from the suture plane.

*Ridges*.—Very narrow, a small ridge near groove on each side of suture.

*Tendency to split*.—None.

*Color*.—Varies from 2.5Y 4/4 to 2.5Y 5/4 when dry.

Kernel:

*Size*.—Large. Average length 20.6 mm. Average width 12.9 mm. Average depth 7.7 mm.

*Form*.—Ovoid.

*Viability*.—Viable, complete embryo development.

*Skin color*.—Varies from 2.5Y 8/4 to 5Y 8.5/4.

Use:

*Dessert*.—Market — local and long distance.

Keeping quality: Good, held firm in cold storage at 38° to 42° F. for 3 weeks without internal breakdown of flesh or appreciable loss of flavor.

Shipping quality: Good, showed minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

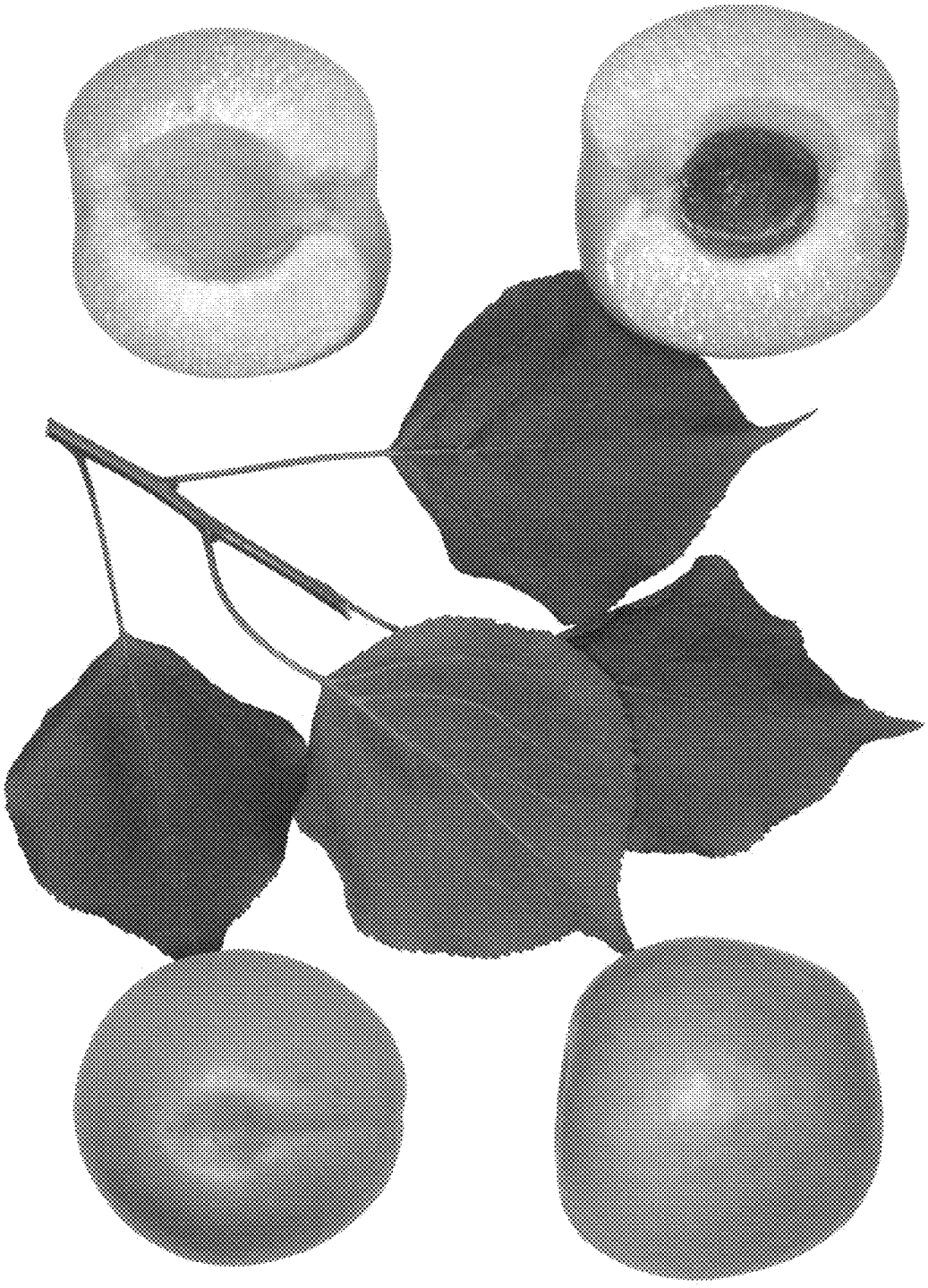

* * * * *